United States Patent [19]

Aarts

[11] Patent Number: 4,871,057

[45] Date of Patent: Oct. 3, 1989

[54] METHOD OF, AND APPARATUS FOR, TEMPORARILY REMOVING A PRODUCT FROM A SERIES OF PRODUCTS BEING TRANSPORTED

[75] Inventor: Mathias L. C. Aarts, Bilthoven, Netherlands

[73] Assignee: Product Suppliers AG, Zug, Switzerland

[21] Appl. No.: 130,690

[22] Filed: Dec. 9, 1987

[30] Foreign Application Priority Data

Dec. 17, 1986 [NL] Netherlands ........................ 8603210

[51] Int. Cl.[4] ........................................ B65G 47/00

[52] U.S. Cl. ................................ 198/346.1; 198/347; 198/465.1; 29/33 P

[58] Field of Search .................. 198/346.1, 347, 465.1, 198/465.2, 465.4; 29/33 P, 563; 414/222, 403, 404

[56] References Cited

U.S. PATENT DOCUMENTS 4,316,754 2/1982 Hinchcliffe et al. ................ 198/347

4,398,630 8/1983 Brems ................................ 198/465.1

4,704,792 11/1987 Itagaki et al. ....................... 414/222

FOREIGN PATENT DOCUMENTS 111745 6/1984 European Pat. Off. ............ 198/347

1531898 11/1970 Fed. Rep. of Germany .

8397 1/1977 Japan .................................. 198/347

188222 9/1985 Japan .................................. 198/347

*Primary Examiner*—Joseph E. Valenza

*Attorney, Agent, or Firm*—Scully, Scott, Murphy & Presser

[57] ABSTRACT

For temporarily removing a product from a series of products supplied by a supply conveyor, the product is taken over by a movable carrier placed in a starting position in the vicinity of the supply conveyor. The carrier with the product is then removed from the conveyor, for example, for the product to be subjected to a treatment. After the treatment, the carrier with the product is returned to the starting position, where the product is placed on a discharge conveyor while simultaneously a next product from the supply conveyor is placed onto the carrier.

9 Claims, 7 Drawing Sheets

23a 22a 12a 11 25 24 16a 16b 26 12b 27 22b 23b 13
14b
12
10
11
14a 12
13
14b
12
10
14a
11

12
13
12
10
11

14

METHOD OF, AND APPARATUS FOR, TEMPORARILY REMOVING A PRODUCT FROM A SERIES OF PRODUCTS BEING TRANSPORTED

BACKGROUND OF THE INVENTION

1. Field of the Invention

This invention relates to a method of, and apparatus for, temporarily removing a product from a series of products being transported, for example, for subjecting the product to a treatment.

More particularly, the invention relates to a method of temporarily removing a product from a series of products being successively supplied by a supply conveyor, in which the product to be removed is taken over from said supply conveyor by a movable carrier disposed in a starting position in the vicinity of said supply conveyor, the carrier with the product is removed from the starting position, and thereafter the carrier with the product is returned to the starting position, where the product is placed from the carrier back into the series.

2. Discussion Of The Prior Art

A method of this kind is described in German patent No. 1,531,898. That patent describes a method of transporting cases, boxes and the like, supplied by a roller conveyor to storage racks disposed along one side of the roller conveyor. For this purpose, the roller conveyor has a segment that is movable transversely to the roller track to a given storage rack. Placed within the roller supply path, the segment constitutes a portion of the supply path. When an object carried by the roller track must be transported to the store, the segment with the object on it is moved transversely to the supply track to the storage rack in question, where the object is removed from the roller segment and stored in the rack. The roller segment is coupled to a second roller segment which when the first is removed from the supply track takes its place in the supply track, thereby maintaining the continuity of the supply roller track. For moving the objects over the roller track segments, the rollers thereof are driven by motors mounted on the segments. The segments can also be used the other way around for returning an object from the rack to the conveyor. For supplying an object from the conveyor to a given rack, it is necessary that, of a coupled pair of roller segments, the leading segment (as viewed in the direction of movement to the rack) carries the object from the supply path, and the trailing segment occupies the place left in the conveyor. When the object has been transferred from the segment to the rack, the pair of segments must be returned into their original position relative to the conveyor before another object can be transferred from the conveyor to the same rack. The reverse applies when objects are to be returned from a given rack to the conveyor. The prior apparatus is therefore in essence only suitable for removing goods incidentally supplied by a roller conveyor, in particular for transporting goods to different storage racks, with each rack being serviced by its own pair of roller segments. The rollers of the pairs of segments are driven by motors for passing an object supplied by the roller track onto or over the roller segment, or returning an object from the rack, carried by the segment, back onto the main roller conveyor.

SUMMARY OF THE INVENTION

It is an object of the present invention to provide a method of the above kind which is suitable for use with an uninterrupted series of supplied articles, which can be carried out efficiently and rapidly, and has a high degree of flexibility as regards the number of articles to be removed from the series, and even permits removing successively each of the articles supplied from the supply conveyor at a high rate and at the same place.

For this purpose, the method according to the invention is characterized in that, in the starting position of the carrier, the product is transferred from the carrying surface of the carrier to a discharge conveyor simultaneously with, or substantially simultaneously with, the transfer of a next product from the supply conveyor to the carrier.

According to the invention, two operations are carried out simultaneously, namely, returning an article removed at an earlier stage to the discharge conveyor (normally located in line with the supply conveyor) and placing a next supplied article on the carrier in the starting position.

The invention also provides apparatus for temporarily removing a product from a series of products being transported in accordance with the above method, comprising a supply conveyor for supplying a series of successive products; a movable carrier for taking over the product to be removed from the series in a starting position in the vicinity of the supply conveyor; and moving means for removing the carrier with product from the starting position and thereafter returning the carrier with product to the starting position for placing the product from the carrier back into the series at that position, said carrier having a carrying surface for carrying the product, which carrying surface, in the starting position of the carrier, forms a common portion of a carrier track to be traversed by the carrying surface with the carrier, and a conveyor track crossing said carrier track for conveying the products between the supply conveyor and a discharge conveyor separate therefrom, characterized in that the carrier track is an endless track.

The temporary removal of the product can serve any desired purpose. Usually, the removal will serve to treat the product, for example, a package or its contents. The treatment may comprise checking, testing, painting, re-arranging, sorting the products, and the like, or mounting or removing a part. Both the supply conveyor and the discharge conveyor commonly take the form of a conveyor belt or conveyor chain, but other forms are possible.

The carrier moves along a track which comprises a starting position, i.e. a position close to the supply conveyor where the product to be removed is placed on the carrying surface of the carrier. The product may be placed on, and subsequently removed from, the carrier using suitable handling means, for example, grippers, pushing arms, and the like disposed in the vicinity of the starting position. In the starting position, the carrier may be arranged so that the product just slides from the moving supply conveyor onto the carrying surface of the carrier. For example, in the starting position, the carrier may be placed in front of the foremost end of the supply conveyor, with the latter taking the form of a conveyor belt, in such a manner that the carrying surface is at the same level as, or at a somewhat lower level than, the foremost belt portion. In this arrangement, the use of particular handling means is unnecessary.

If desired, two or more products may be successively placed on the carrying surface in the same starting position of the carrier. Also, if desired, from its starting position, the carrier may be shifted a little to a second, and if necessary subsequent starting positions for receiving further products in addition to those already received. Naturally, the size of the carrying surface should be adapted to the use contemplated.

When the carrier has received the product, the carrier is removed from the starting position, whereafter various further steps are possible. One possibility is for the carrier with product, during its movement along the carrier track, to reach a discharge station where the product is removed from the carrying surface for it to be subjected to a treatment in a treating device. After the treatment, the product is placed back on the carrier or placed on another carrier disposed at that position, in a loading station also located on the carrier track. Possibly, the loading station is at the same position along the carrier track as is the unloading station.

Another possibility is for the product to be subjected to a treatment as it is located on the carrier. During the treatment, the carrier may be stationary or continue to move along the track to be traversed.

Irrespective of the nature and manner of treatment, the treated product is placed back onto the carrier (or, if a plurality of carriers are provided, one of the carriers), if it has not remained on the carrier during the treatment. During the further cycle of the carrier, the latter returns to its starting position, where now the treated product is delivered to the discharge conveyor, and a fresh product can be put on the carrier.

The carrying surface of the carrier not only forms a portion of the carrier track to be traversed by the carrying surface with the carrier, but also, in the starting position of the carrier, a portion of the (direct) connecting track between the supply conveyor and the discharge conveyor, which crosses the carrier track. As a result of this construction, the carrier can each time be used for one of two purposes in the starting position. One possibility is that, in the starting position, the carrier just serves as a connection for the direct passage of products supplied by the supply conveyor to the discharge conveyor. So long as this direct transfer remains desirable, the carrier is kept in the starting position, and no articles are removed from the series of products.

The other possibility, already referred to, is that a product is transferred from the supply conveyor to the carrier and the carrier together with the product is removed from the starting position over the carrier track.

By virtue of this possibility of selection, any or all of the products supplied can be either removed from the series or transferred direct to the discharge conveyor as desired. Flexible operation is possible by using two or more carriers traversing a common carrier track. One of the carriers may be in the starting position, either to serve as a link between the two conveyors, or for receiving a next product to be removed from the series, while the other carriers may be in other positions in the carrier track. In this way it is possible for one or more specimens to be removed from the supplied stream of products, either regularly or incidentally, and for the other products to be immediately passed to the discharge conveyor. In addition, a choice can be changed at any moment. The movement of the carrier over the carrier track may be a to-and-fro movement, but alternatively the carrier track is formed as a circuit along which a series of carriers move in succession. In another possible embodiment, one or more carriers traverse separate carrier tracks. In that arrangement, two carriers, i.e. one from each carrier track, will always be simultaneously in a starting position and their carrying surfaces will together form a direct link between two conveyors.

The carrier may take the form of a belt conveyor whose surface forms one or a series of carrying surfaces. Preferably, the carriers are each formed as a separate unit movable along rails or other guide means. Each carrier may carry an identifying code that can be detected, for example, by an electric eye coupled to a control apparatus which monitors and, depending on the desired task of the carrier, controls the movement of the carriers.

A particularly suitable apparatus for driving the individual carriers is an electromagnetic linear stepping motor, having co-operating parts disposed in the carrier and in the guide means. In that arrangement, the coils serving for generating a magnetic field may be housed stationarily in the guide track, and the armatures, formed as soft iron plates, secured to the carriers. By alternately energizing the coils, the carrier can be given the desired movement, or fixed in a stationary position.

An important advantage of the present invention is that particular facilities for placing products on and removing products from, the carrier, with appurtenant control means, can be omitted by using for this purpose the moving series of products supplied by the supply conveyor. The leading product of the supplied series of products is shifted onto the carrier by the travelling supply conveyor, and at the same time the product already present on the carrier is shifted onto the discharge conveyor. In other words, in one operation, a product is shifted onto the carrier and the preceding one is removed from it. It will be clear that this product removed from the carrier may be either a product removed earlier from the series and transported over the carrier track, or a preceding product in the series to be passed direct from the supply conveyor to the discharge conveyor.

If necessary, support means or guide means, such as rails, are provided along the sides at the end of the supply conveyor and the beginning of the discharge conveyor to cause a product to shift onto and from the carrier without failure. Similar means may be mounted on the carrying surface of the carrier.

The carrier may further be provided with means for fixing the product placed on it, such as clamping means. These may take the form of pneumatic bellows capable of holding the product on opposite sides, and possibly causing the product to occupy a desired position relative to the carrying surface. Clamping the product on the carrier is generally desirable when the product is to be subjected to a treatment on the carrier.

In many cases it will be possible for the supply conveyor to run continuously at a constant rate as the method is carried out. In particular this will be possible if the time interval between removing a carrier with product from the starting position and re-placing this carrier (or placing a next carrier) into the starting position is short relative to the time interval in the supply of a next product, by the supply conveyor.

In other cases, it may be necessary to interrupt the delivery of products by the supply conveyor during the interval when no carrier is in the starting position. This may be done, however, without interrupting, or even delaying, the main stream of products on the supply conveyor by forming the foremost part of this conveyor as a separate auxiliary conveyor. This auxiliary conveyor is given a higher transport velocity than the main conveyor, but is stopped during the change of a carrier in the starting position. All this is effected in such a manner that the average velocity of the auxiliary conveyor is at least equal to the constant velocity of the main conveyor.

BRIEF DESCRIPTION OF THE DRAWINGS

Some embodiments of the invention will now be described, by way of example, with reference to the accompanying diagrammatic drawings. In said drawings.

DETAILED DESCRIPTION OF THE PREFERRED EMBODIMENTS

Figure 1A:
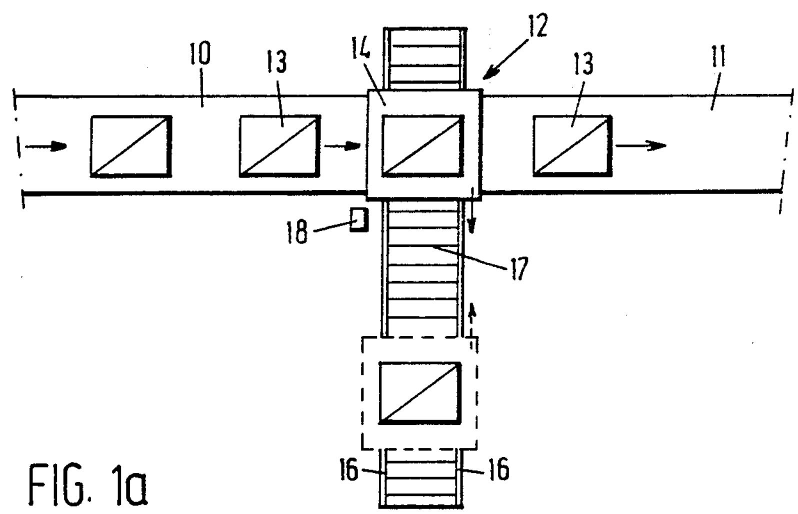
FIG. 1*a* and 1*b* show an apparatus according to the present invention with a carrier moving to and fro, in top plan view and side-elevational view, respectively.
Figure 1B:
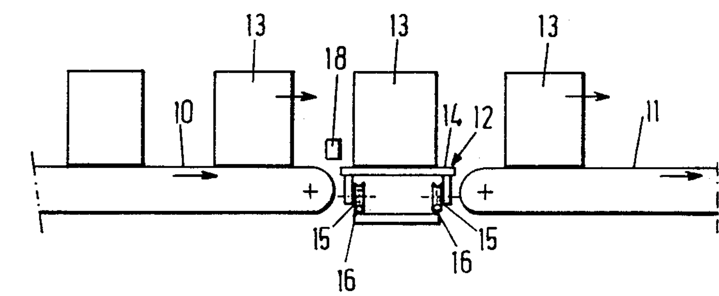

FIGS. 1*a* and 1*b* show a supply conveyor 10 and a discharge conveyor 11, both here taking the form of conveyor belts transporting packages 13. A carrier 12 travels on wheels 15 over rails 16 extending transversely to the direction of movement of the conveyor belts. Carrier 12 is an independent unit, driven by a linear stepping motor, having pole-shoes 17 extending transversely to rails 16, and including a plurality of soft iron strips, serving as an armature, provided at the bottom of the carrier to extend in the same direction as the pole-shoes. In the figures, the carrier is in the starting position located between the two conveyor belts, in which the carrying surface 14 of the carrier is capable of receiving a package from the supply belt.

When the apparatus is in use, packages 13 are regularly and serially supplied by belt 10. The foremost package on supply belt 10 is shifted by the belt onto the carrying surface 14 of the carrier, which surface is at the same level as the belt. When the carrier remains in the starting position during the supply of subsequent packages from the supply belt, the package on the carrier is pushed on by the next package towards and onto the discharge belt 11. In this situation, the carrying surface 14 of the carrier simply serves as a link track between the two belts 10, 11. If, on the other hand, the package 13 on the carrier should be temporarily removed from the series of packages, the pole-shoes 17 of the linear stepping motor are successively energized, as a result of which the carrier is rolled to a final position indicated in dotted lines. In that position the package is removed from the carrier, for example, by a pick-up device circulating over this point, which carries the package to a treating device or constitutes itself a part of a treating device.

After the treatment, the package is put back onto the carrier in the end position thereof. If desired, the package is treated on the carrier proper in its end position. Yet another possibility is for the package to be treated on the carrier after the carrier with the package has been removed from the end position, and subsequently, after the package has been treated, the carrier with the treated package is re-placed in the end position.

Finally the carrier with the treated package is returned to the starting position. In that position the treated package is pushed off the carrier onto the discharge belt by the now-foremost package on the supply belt. Thus the treated package has been returned to the main stream of the packages.

This procedure can be regularly repeated with packages being subjected to the treatment or passed direct from the supply belt to the discharge belt as desired.

The movements of the carrier are monitored by an electric eye 18, which is connected to automatic computer-aided control equipment.

Generally speaking, after the package has been removed from the carrier in the end position on the rails, the carrier will move back and forth to the starting position once or several times for supplying next packages to be treated or for discharging earlier treated packages. The supply belt 10 travels at a constant velocity, but if this velocity is relatively high, it may be desirable for the leading end of the belt to be formed as a separate auxiliary belt which if there is no carrier in the starting position is stopped but before and after this travels at a higher velocity than the main supply belt. This can be controlled in such a manner that the average velocity of the separate auxiliary supply belt is equal to, or higher than, the velocity of the main supply belt. The discharge belt can travel at a constant velocity.

When an auxiliary supply belt is used, the procedure is as follows:

(a) the electric eye 18 detects that a carrier is in the starting position;

(b) the stationary auxiliary belt is actuated;

(c) the eye detects that a package is on the carrier;

(d) the programmed control computer determines whether the package has to be removed from the series, and if so, then (e) the auxiliary belt is stopped;

(f) the carrier with the package to be treated is moved to the end position on the rails; and (g) the carrier (or another carrier) with a treated package is returned to the starting position.

Figure 2:
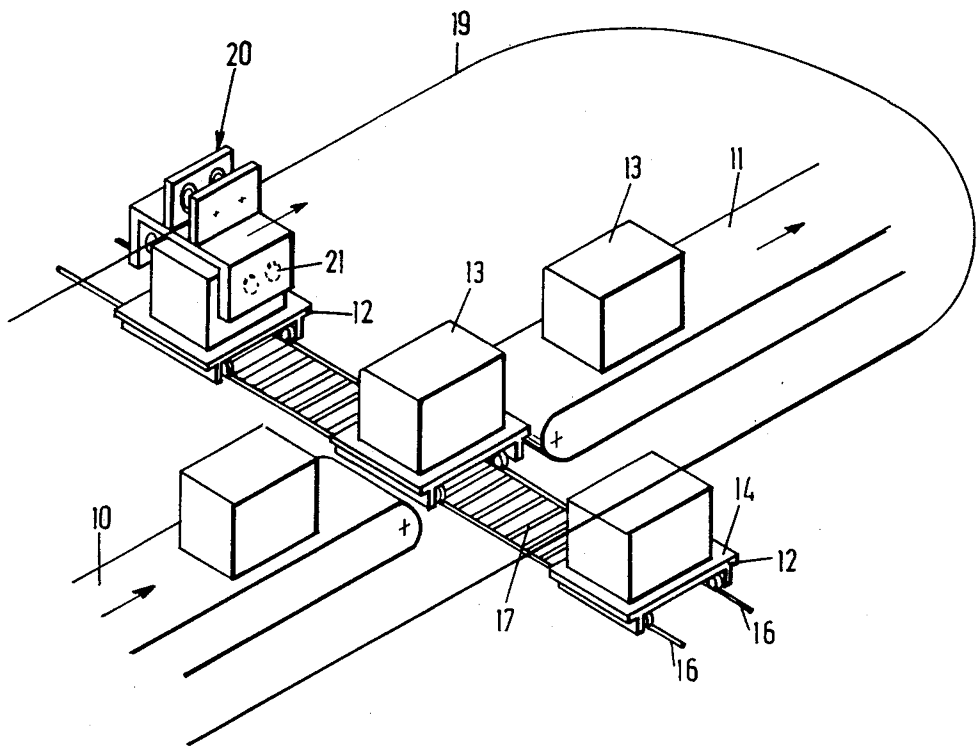
FIG. 2 shows, in perspective view, an apparatus according to the present invention with one or more carriers.

Various variations of the embodiment of FIG. 1 are possible. Thus FIG. 2 shows an embodiment in which the package to be treated is removed from the carrier in a discharge position of the carrier and, after having been treated, is returned to the carrier in a separate loading position. The discharge and loading positions of the carrier are on opposite sides of the starting position (on the left and right hand side in FIG. 2, respectively). In FIG. 2, the carrier is shown in each of the three positions it can take. FIG. 2 further shows a clamping arm 20 arranged to travel over a track 19, and adapted to take a package from the carrier in the discharge position thereof by means of clamping elements 21, which can be activated, and carry it to a treating device located along track 19 (and not shown). After the treatment, the package is again put on the carrier at the loading point located opposite the discharge point.

The apparatus of FIG. 2 may be formed with a single carrier which successively occupies the starting position, the discharge position, the loading position, and again the starting position. Along track 19, however, a plurality of clamping arms 20, and possibly a plurality of treating devices may be provided, in which arrangement the end positions located on opposite sides of the starting position of the carrier may alternately function as unloading and loading positions.

Clamping arm 20 may also be arranged to lift the package to be treated together with the carrier from rails 16 at an end thereof and carry it over track 19 for treatment of the package. Subsequently, the carrier with the package is put back on the rails at the other end. In particular in the last-mentioned case, it is of advantage to use a series of successive carriers.

Figure 3:
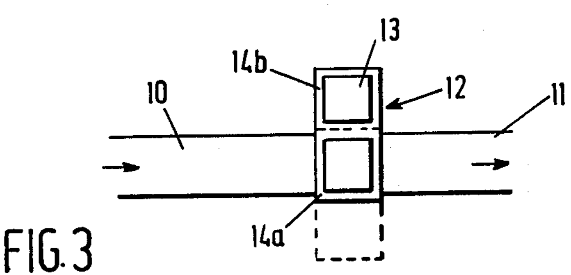
FIGS. 3–9 show various embodiments of the present invention.

FIG. 3 illustrates the principle of an embodiment in which the carrier 12 moves back and fro between two positions in each of which, alternately, a carrying surface of the carrier is in a starting position and a second carrying surface in an end position. In the position shown, carrying surface 14*a* receives a package from supply belt 10, and the package placed earlier on carrying surface 14*b* is removed from the carrier for treatment and after treatment is put back on it. The package may alternatively be treated on the carrying surface 14*b* proper. Subsequently, the carrier 12 is placed in the position shown by a dotted line, in which a fresh package is shifted onto carrying surface 14*b* by supply belt 10, whereby the treated package is shifted from carrying surface 14*b* onto discharge belt 11. In that position, the package on carrying surface 14*a* is also treated in the same way as described hereinbefore with respect to the package on carrying surface 14*b*.

Figure 4:
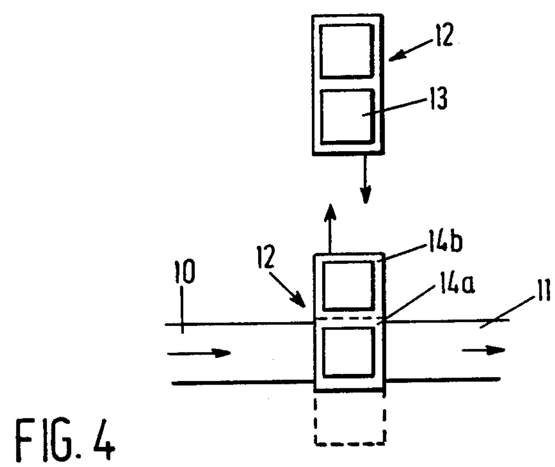

In the embodiment of FIG. 4, carrier 12 occupies two successive starting positions. In the first position, indicated by a dotted line, carrying surface 14*b* receives a package, while a package already present on it is shifted onto discharge belt 11. In the second starting position of the carrier, shown by solid lines, the same is effected with respect to carrying surface 14*a*. The carrier with the packages is now removed from the starting position, and the packages are subjected to a treatment, either on the carrier or not. Thereafter, the carrier with the treated packages is returned to the position shown in dotted lines, whereafter the cycle is repeated.

If desired, the carrier 12 may be extended to receive a third or subsequent packages in a third or subsequent starting position.

Figure 5:
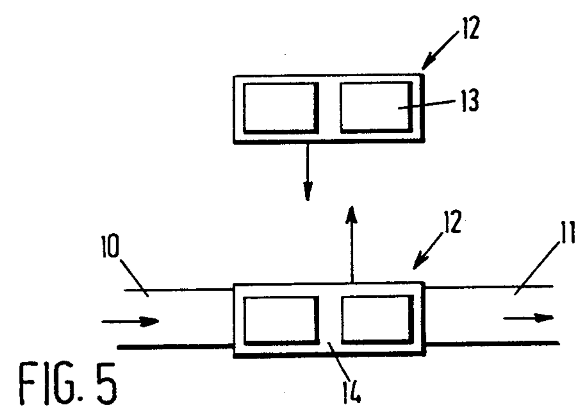

In FIG. 5, the carrier has a starting position in which, in succession, two packages are moved from supply belt onto carrying surface 14, and at the same time two treated packages present on carrying surface 14 are shifted onto discharge belt 11. Subsequently, the carrier is moved to an end position for treatment of the packages in a similar manner as described with reference to FIG. 4. Thereafter the carrier returns to the starting position for repeating the cycle. The system of FIG. 5 can also be extended to enable the carrier to receive three or more packages from supply belt 10 in its starting position.

Figure 6:
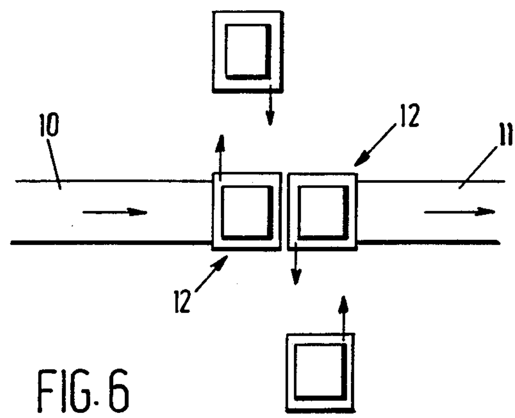

In FIG. 6, two carriers 12 are used, which each traverse their own track, but are simultaneously in their starting position. In that position, the carriers each receive a package from supply belt 10, while the two treated packages already present on the carriers are passed to discharge belt 11.

Figure 7:
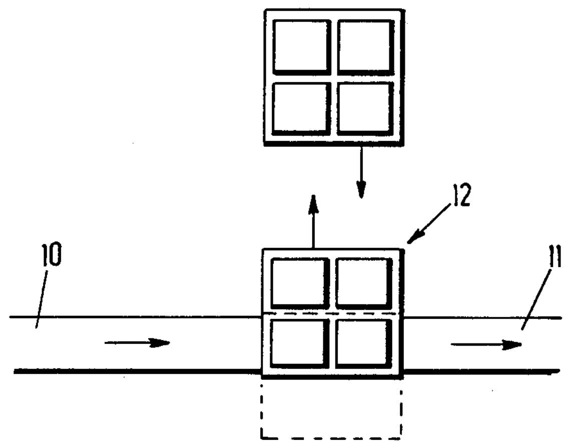

FIG. 7 shows a combination of the systems of FIGS. 4 and 5, in which, in a starting position, the carrier receives two packages (and gives two packages to the discharge belt), and this takes place again in a second starting position.

Although the carriers have been described, with reference to the basic diagrams of FIGS. 4–7, as travelling to and fro, it will be clear that each carrier can traverse a circuit, and in each circuit a series of successive carriers can be used, one of which is successively in the starting position. In the embodiment of FIG. 6, the carriers can traverse the two carrier tracks in a manner in which the two carriers leave the starting position in the same direction or, as shown, in opposite directions. The system of FIG. 6 can also be extended by more than two carrier tracks, in which, each time, a carrier in one carrier track is in its starting position simultaneously with a carrier in each other carrier track.

Figure 8:
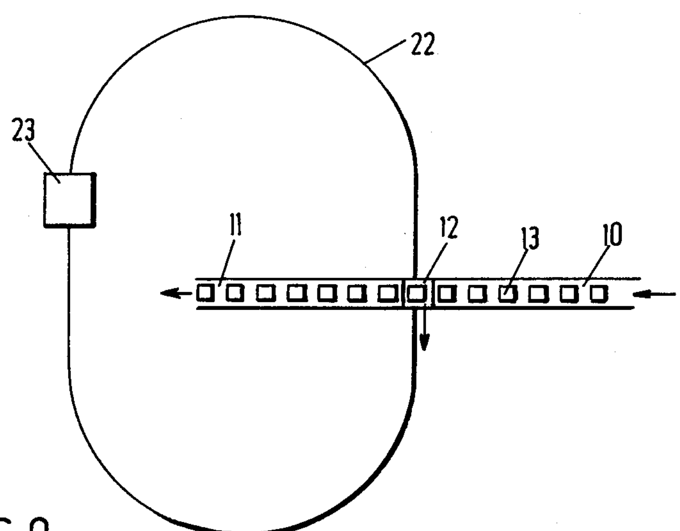

FIG. 8 shows a scheme in which carrier 12, shown in its starting position, traverses a circuit 22. The package to be treated is passed with the carrier from the starting position along circuit 22, thereby passing a treating device 23, where the package is treated. The carrier with the treated package continues its way along the circuit, thereby returning into its starting position where the carrier receives a fresh package and the treated package is put onto the discharge belt.

Figure 9:
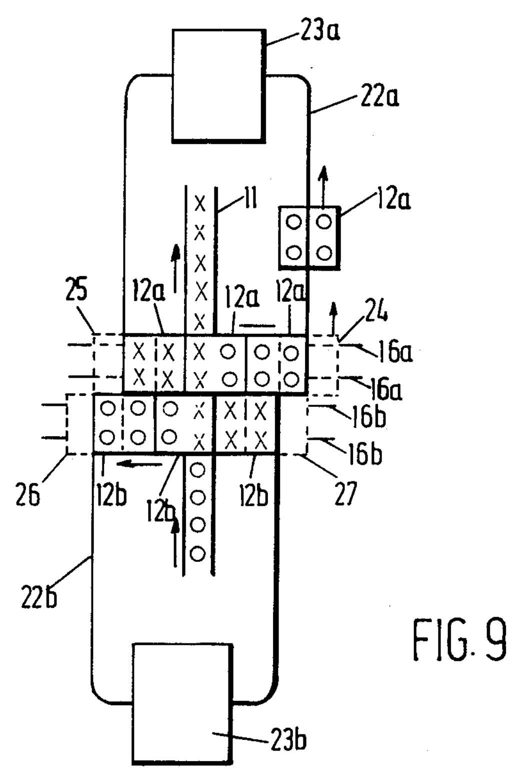
Figure 10A:
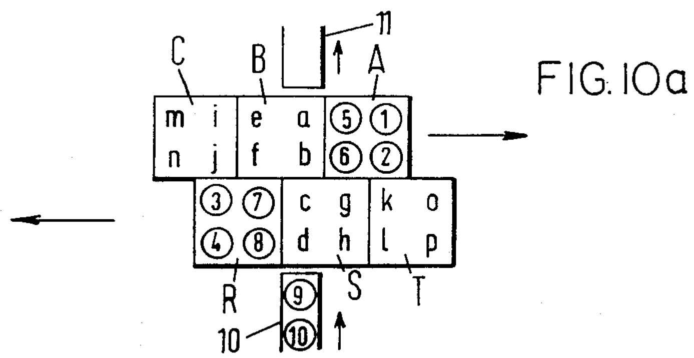
FIG. 10*a*–*g* show a scheme of successive positions of carriers in the embodiment of FIG. 9.
Figure 10B:
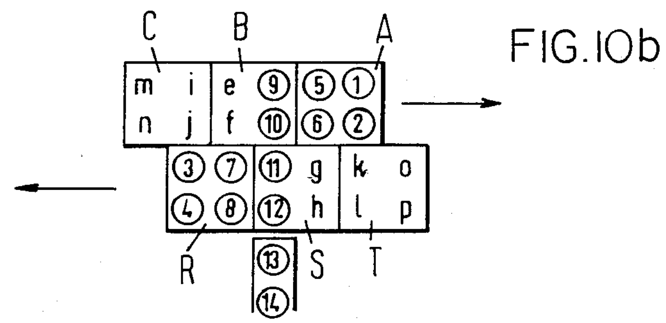
Figure 10C:
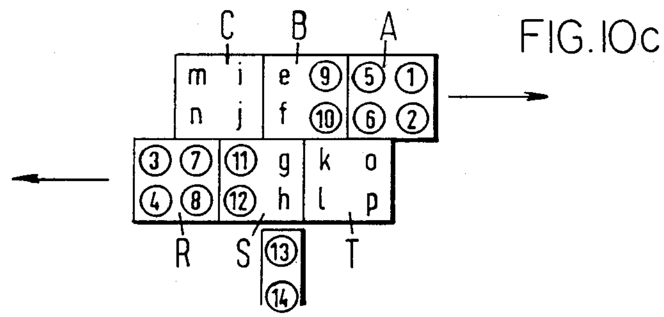
Figure 10D:
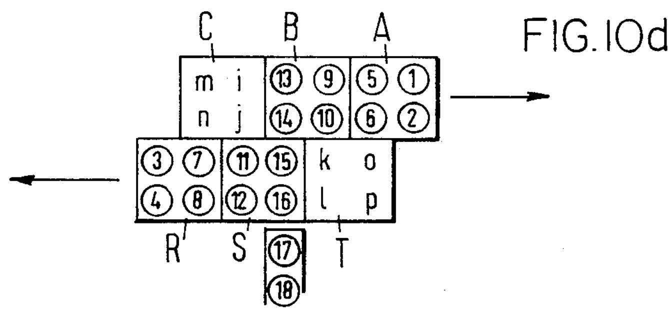

FIG. 9 shows a combination of the systems illustrated in FIGS. 6 and 7, in which two separate carrier circuits are provided, which are each traversed by a plurality of successive identical carriers. Circuit 22*a* with treating device 23*a* is traversed by successive carriers 12*a*, and circuit 22*b* with treating device 23*b* is traversed by carriers 12*b*. Untreated packages are designated by "O", and treated packages by "X". There are always at least three carriers 12*a* on rails 16*a* and also at least three carriers 12*b* on rails 16*b*. Periodically, one of carriers 12*a* is in a starting position. This carrier is moved incrementally to the right to reach in the end an end position 24, indicated by dotted lines, on rails 16*a*. In this end position 24, carrier 12*a* with packages is lifted off the rails and put on circuit 22*a*. Carrier 12*a* then traverses treating device 23*a* and finally, with the treated packages, reaches the other end position 25 on rails 16*a*. Here the carrier 12*a* is again placed on rails 16*a*, and subsequently moved in incremental steps to the starting position, where fresh packages are placed on the carrier and the treated packages are removed. Carriers 12*b* function in a similar manner and after the starting position first, to the left, reach the end position 26, then via circuit 22*b* and treating device 23*b* reach the other end position 27, and finally, over rails 16*b*, return to their starting position. The successive stages in the movement of carriers 12*a*, b of FIG. 9 over the rails are illustrated in the scheme of FIGS. 10*a–g*. In this figure, the packages to be treated are designated by encircled numerals, and the packages treated by small letters. FIG. 10*a* shows three carriers 12*b* designated by capital letters A, B, C, and three carriers 12*b* designated by capital letters R, S, T. Carriers B and S are in a first starting position and together contain four treated packages a, b, c, d to be discharged at this instant. In FIG. 10*b*, these packages have been discharged to discharge belt 11 and replaced by four fresh packages 9–12. Carriers A, B, C are now together moved one increment to the right, and at the same time carriers R, S, T are together moved one increment to the left (FIG. 10*c*; also see FIG. 9). Carriers B and S are now in the second starting position, where treated packages e, f, g, h are discharged and four fresh packages 13–16 are placed on the carriers (FIG. 10*d*).

Figure 10E:
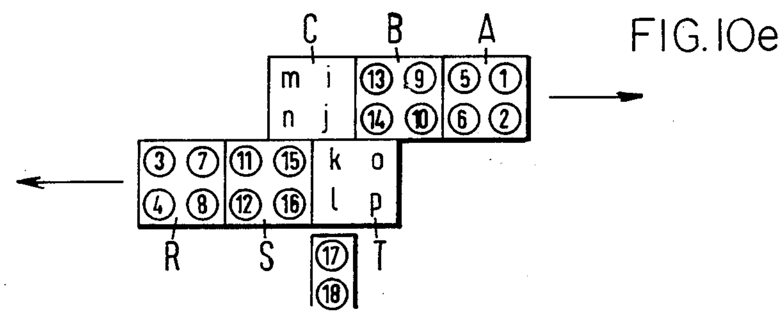
Figure 10F:
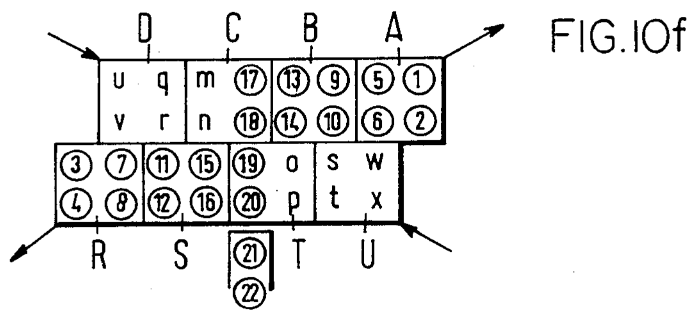
Figure 10G:
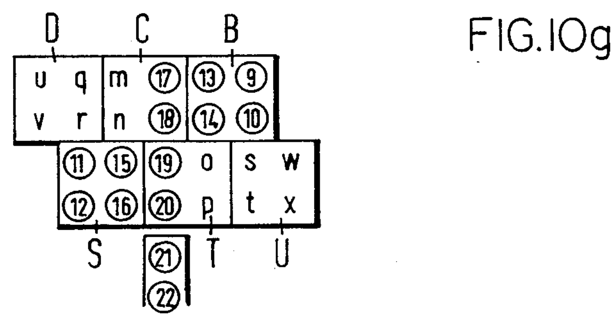

After another increment to the right of carriers A, B, C and to the left of carriers R, S, T, carriers C and T are now in the first starting position (FIG. 10*e*). In this position, packages i, j, k, l are removed from carriers C, T to the discharge belt and replaced by packages 17-20 (FIG. 10f). In this position, carriers A and R with untreated packages are also removed from the rails (in positions 24 and 26, respectively in FIG. 9) and carriers D and U with treated packages are placed on the rails (in positions 25 and 27, respectively in FIG. 9). The situation then is as shown in FIG. 10g, and this, in turn, is in principle the same situation as in FIG. 10b. The steps are then repeated with successive carriers.

What I claim is:

1. Apparatus for temporarily removing each product from a series of products being transported on a conveyor line comprising: a supply conveyor for supplying a series of successive products; a discharge conveyor; a movable carrier for taking over the product to be removed from the series in a starting position in the vicinity of the supply conveyor; and moving means for removing the carrier with product from the starting position and thereafter returning the carrier with product to the starting position for putting the product from the carrier back into the series at that position, said carrier having a carrying surface for carrying the product, said carrying surface forming a common portion of a carrier track at said starting position which is to be traversed by the carrying surface and the carrier, and the conveyor line crossing said carrier track in line with said supply conveyor and said discharge conveyor for conveying the products between the supply conveyor and the discharge conveyor, wherein said moving means returns said carrier and product to said starting position to return said product to said series while said carrier simultaneously takes over a subsequent product for removal from said series, said carrier track being an endless track.

2. Apparatus as claimed in claim 1, wherein at least two endless carrier tracks having parallel portions extending side by side with each other and to be traversed by the carriers in the vicinity of their starting positions are provided.

3. Apparatus as claimed in claim 1, wherein the means for moving the carrier comprise an electromagnetic linear stepping motor having cooperating parts disposed in the carrier and in the guide means.

4. A method of temporarily removing each product from a series of products being successively supplied by a supply conveyor, comprising taking over a product to be removed from said supply conveyor by a movable carrier disposed in a starting position in the vicinity of said supply conveyor and which traverses a closed circuitous track, removing the carrier with the product from the starting position, thereafter returning the carrier with the product to the starting position such that the product is put from the carrier back to the series of products, transferring the product at said starting position from the carrier to a discharge conveyor while simultaneously, or substantially simultaneously, transferring a subsequent product from the supply conveyor to the carrier, wherein the product, both when being taken over by the carrier from the supply conveyor and when being returned from the carrier to the discharge conveyor is transferred to and from an intermediate position in the series of products being transported over the supply and discharge conveyors, subjecting the product removed by the carrier to a treatment process before being returned on the carrier to the starting position of the carrier.

5. A method is claimed in claim 4, wherein one or more of the products are removed from the supply conveyor at regular locations in the supplied series of products.

6. A method is claimed in claim 5, wherein each of the products supplied is removed from the series and thereafter returned to the series.

7. A method as claimed in claim 4, wherein a series of successive carriers are provided and traverse the same circuitous track.

8. A method as claimed in claim 7, wherein at least two carriers each traverse a separate carrier track and simultaneously depart from their starting position.

9. A method as claimed in claim 4, wherein after a product is taken over by the carrier in the starting position, the carrier is moved to a second starting position such that one or more of the immediately following products from the supply conveyor may be taken over before said carrier is removed from the starting position.

* * * * *